(12) United States Patent
Kusumoto

(10) Patent No.: US 8,998,413 B2
(45) Date of Patent: Apr. 7, 2015

(54) MEASUREMENT APPARATUS, OPHTHALMOLOGIC IMAGING APPARATUS, CONTROL METHOD, AND STORAGE MEDIUM

(71) Applicant: Canon Kabushiki Kaisha, Tokyo (JP)

(72) Inventor: Hiroshi Kusumoto, Kokubunji (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/904,802

(22) Filed: May 29, 2013

(65) Prior Publication Data

US 2013/0321769 A1 Dec. 5, 2013

(30) Foreign Application Priority Data

Jun. 1, 2012 (JP) ................. 2012-126195

(51) Int. Cl.
*A61B 3/14* (2006.01)
*A61B 3/02* (2006.01)
*A61B 3/10* (2006.01)
*G01B 11/26* (2006.01)

(52) U.S. Cl.
CPC ............. *A61B 3/1025* (2013.01); *A61B 3/14* (2013.01); *G01B 11/26* (2013.01)

(58) Field of Classification Search
USPC ................................. 351/200–246
See application file for complete search history.

(56) References Cited

U.S. PATENT DOCUMENTS

| | | | |
|---|---|---|---|
| 6,193,372 B1 | 2/2001 | Okumura et al. | |
| 6,337,993 B1 * | 1/2002 | Kishida et al. | 600/476 |
| 6,655,805 B2 | 12/2003 | Fujieda | |
| 7,527,379 B2 | 5/2009 | Yamaguchi et al. | |
| 7,635,186 B2 | 12/2009 | Kobayashi et al. | |
| 7,736,001 B2 * | 6/2010 | Tanaka et al. | 351/214 |
| 8,469,514 B2 | 6/2013 | Utsunomiya | |
| 8,506,081 B2 * | 8/2013 | Matsumoto | 351/214 |
| 8,596,785 B2 * | 12/2013 | Imamura et al. | 351/206 |
| 8,646,915 B2 | 2/2014 | Nozato | |
| 8,708,489 B2 | 4/2014 | Utagawa | |
| 2001/0056239 A1 * | 12/2001 | Ono | 600/476 |
| 2007/0159597 A1 | 7/2007 | Fukuma et al. | |
| 2007/0216866 A1 | 9/2007 | Kobayashi et al. | |
| 2009/0303428 A1 | 12/2009 | Tendler | |
| 2012/0019780 A1 | 1/2012 | Nozato | |
| 2012/0033180 A1 | 2/2012 | Pieri et al. | |
| 2013/0321765 A1 | 12/2013 | Yuasa | |
| 2013/0321766 A1 | 12/2013 | Morohashi | |
| 2013/0321767 A1 | 12/2013 | Hirose | |

(Continued)

FOREIGN PATENT DOCUMENTS

JP 2002-200043 A 7/2002
JP 2003-126042 A 5/2003

(Continued)

*Primary Examiner* — Mohammed Hasan
(74) *Attorney, Agent, or Firm* — Canon U.S.A., Inc. IP Division

(57) ABSTRACT

A measurement apparatus for measuring aberration based on return light of measuring light radiated to an object, includes a light source configured to emit the measuring light, a focusing unit configured to focus the measuring light on the object, an acquisition unit configured to acquire, from a storage unit, information indicating a state of the focusing unit corresponding to identification information of a specific object, and a control unit configured to control the focusing unit based on the acquired information indicating the state of the focusing unit.

20 Claims, 9 Drawing Sheets

(56) References Cited

U.S. PATENT DOCUMENTS

2013/0321768 A1 12/2013 Utagawa
2013/0321771 A1 12/2013 Yuasa
2014/0063507 A1 3/2014 Borycki et al.

FOREIGN PATENT DOCUMENTS

| | | |
|---|---|---|
| JP | 2004-033275 A | 2/2004 |
| JP | 2010-259543 A | 11/2010 |

* cited by examiner

MEASUREMENT APPARATUS, OPHTHALMOLOGIC IMAGING APPARATUS, CONTROL METHOD, AND STORAGE MEDIUM

BACKGROUND OF THE INVENTION

1. Field of the Invention

The present invention relates to an ophthalmologic imaging apparatus, and more particularly to a measurement apparatus used for ophthalmologic examination.

2. Description of the Related Art

A scanning laser ophthalmoscope (SLO), which is an ophthalmologic apparatus using a principle of a confocal laser microscope, performs raster scanning for a fundus with a laser that is imaging light, and acquires a planar image from the intensity of its return light with high resolution at a high speed. Concerning the SLO, there has been developed an adaptive optics SLO (AOSLO) apparatus including an adaptive optical system for measuring aberration caused by a subject's eye by a wavefront sensor in real time, and correcting aberration caused by measuring light generated at the subject's eye or its return light. This system enables acquisition of an image reduced in influence of aberration. Japanese Patent Application Laid-Open No. 2010-259543 discusses a composite apparatus that combines an SLO apparatus, which has a wide angle of view, with an AOSLO apparatus, which has a narrow angle of view and high resolution.

SUMMARY OF THE INVENTION

According to an aspect of the present invention, a measurement apparatus for measuring aberration based on return light of measuring light radiated to an object includes a light source configured to emit the measuring light, a focusing unit configured to focus the measuring light on the object, an acquisition unit configured to acquire, from a storage unit, information indicating a state of the focusing unit corresponding to identification information of a specific object, and a control unit configured to control the focusing unit based on the acquired information indicating the state of the focusing unit.

Further features of the present invention will become apparent from the following description of exemplary embodiments with reference to the attached drawings.

BRIEF DESCRIPTION OF THE DRAWINGS

FIG. 1A being a top view of the ophthalmologic imaging apparatus, and FIG. 1B being a side view of the ophthalmologic imaging apparatus.

DESCRIPTION OF THE EMBODIMENTS

Figure 1A:
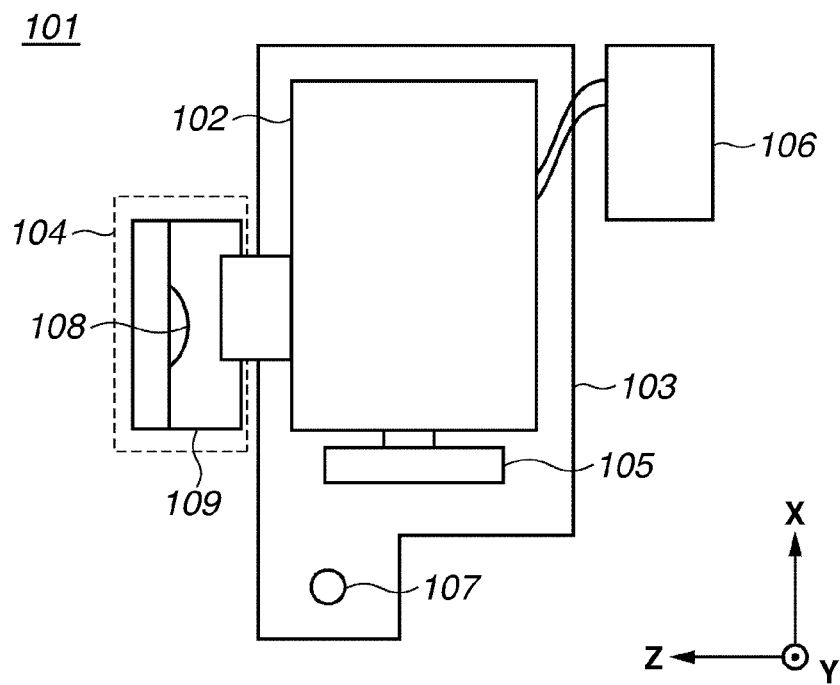
FIGS. 1A and 1B illustrate an appearance configuration of an ophthalmologic imaging apparatus according to an exemplary embodiment.

In the case of imaging performed in an AOSLO apparatus that can acquire high-definition images, there is a possibility that a value of aberration may vary between the time of aberration measurement and the time of imaging. It is, therefore, desirable to shorten adjustment before the imaging.

In this case, when images of the same object are captured many times, in addition to adjustment for normal imaging, adjustment for measuring the same region as that of last imaging must be performed, creating a possibility of time and labor.

According to an exemplary embodiment of the present invention, a measurement apparatus for measuring aberration based on return light of measuring light radiated to an object includes a light source configured to emit the measuring light, a focusing unit configured to focus the measuring light on the object, an acquisition unit configured to acquire information indicating a state of the focusing unit (e.g., the position of a focus lens in an optical axis) corresponding to identification information of a specific object, and a control unit configured to control the focusing unit based on the acquired information indicating the state of the focusing unit (e.g., to move the focus lens along the optical axis).

This enables quick capturing of a high lateral resolution planar image of an object measured for aberration at a desired position.

Exemplary embodiments of the present invention will be described with reference to the attached drawings.

An AOSLO apparatus according to the exemplary embodiment of the present invention will be described.

The AOSLO apparatus according to the present exemplary embodiment, which includes an adaptive optical system, captures a high lateral resolution planar image (AOSLO image) of a fundus. In this apparatus, aberration is measured by a wavefront sensor 255 based on return light of beacon light (measuring light) 206-3 radiated to an object. Further, the apparatus includes a light source 201-3 for generating the measuring light 206-3 to measure the aberration, a focus lens 235-16 for focusing the measuring light 206-3 on the object, and an image capturing parameter acquisition unit 404 for acquiring, from a storage unit 410, an image capturing parameter such as information indicating a state of the focus lens 235-16 corresponding to identification information of a specific object. A focus control unit 406 then controls, based on the acquired image capturing parameter, a position of the focus lens 235-16 to irradiate the specific object with the measuring light 206-3.

For the purpose of assisting the acquisition of the AOSLO image, the AOSLO apparatus can include a WFSLO unit for capturing a wide field angle planar image (WFSLO image), an anterior segment observation unit for recognizing an incident position of imaging light, and a fixation lamp display unit for guiding a line of sight to adjust an imaging place.

In the present exemplary embodiment, a spatial light modulator is used as the adaptive optical system, and the planar image can be acquired by correcting optical aberration caused by a subject's eye. Thus, a good planar image can be acquired irrespective of a diopter of the subject's eye or the optical aberration caused by the subject's eye.

In the present exemplary embodiment, the AOSLO apparatus includes the adaptive optical system to capture a high lateral resolution planar image. However, the adaptive optical system is unnecessary as long as the configuration can realize high resolution.

<Overall Configuration of Apparatus>

Figure 1B:
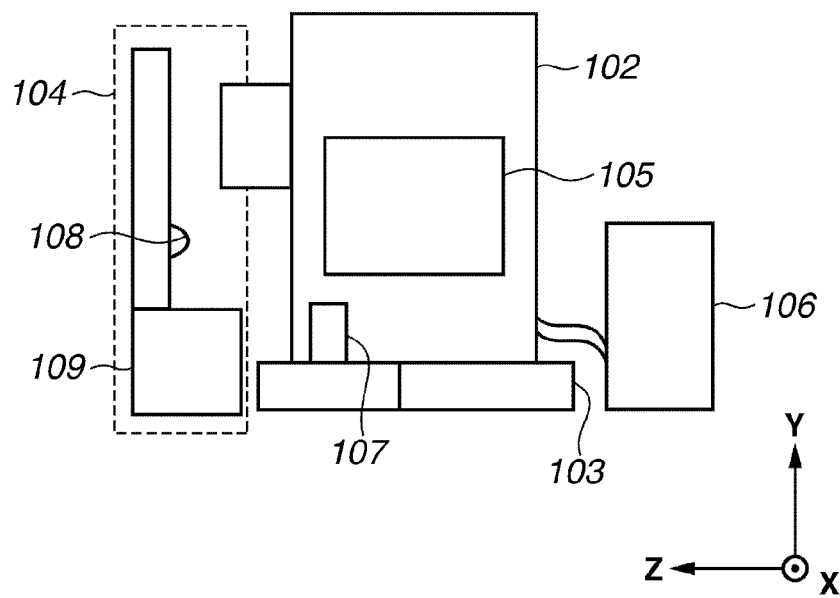

Referring to FIGS. 1A and 1B, an appearance configuration of the AOSLO apparatus 101 according to the present exemplary embodiment will be described. FIG. 1A is a top view of the AOSLO apparatus 101 seen from the upper side, and FIG. 1B is a side view of the AOSLO apparatus 101 seen from the side face.

The AOSLO apparatus 101 includes a light source for measuring aberration, a head unit (measurement unit) 102 including an optical system such as a light source for AOSLO imaging or a focus lens, a stage unit 103 for moving the head unit 102 horizontally or vertically, a face receiver 104 for adjusting a mounting position of a subject's face, a liquid crystal monitor 105 for displaying an operation screen, and a control personal computer (PC) 106 for controlling the entire AOSLO apparatus 101.

The head unit 102 of the AOSLO apparatus 101 includes the focus lens 235-16, the wavefront sensor 255, a spatial light modulator 259, a light source 201-1, a light source 201-2, a focus lens 235-10, a focus lens 235-14, a detector 238-1, a detector 128-2, and a housing for storing these components. The head unit 102, which is installed on the stage unit 103, is horizontally rotated by dropping a joystick 107 so that it can be vertically moved. The face receiver 104 includes a jaw receiver 108 (adjustment unit) on which a jaw is mounted, and a jaw receiver stage unit 109 for moving the jaw receiver 108 horizontally, vertically, or back and forth.

The stage unit 103 constitutes a changing unit for changing a position of the head unit (measurement unit) 102 with respect to the object. The control PC 106 detects and controls an operation amount of the joystick. The jaw receiver stage unit 109 moves a head of the subject detected by the control PC 106 back and forth to secure a focus position, and performs fine adjustment for alignment after the measuring light and the subject's eye have been aligned with each other at the stage unit 103.

The control PC 106 acquires and stores information about the subject in a database in the control PC or an external database through communication from the outside.

<Configuration of Optical System>

Figure 2:
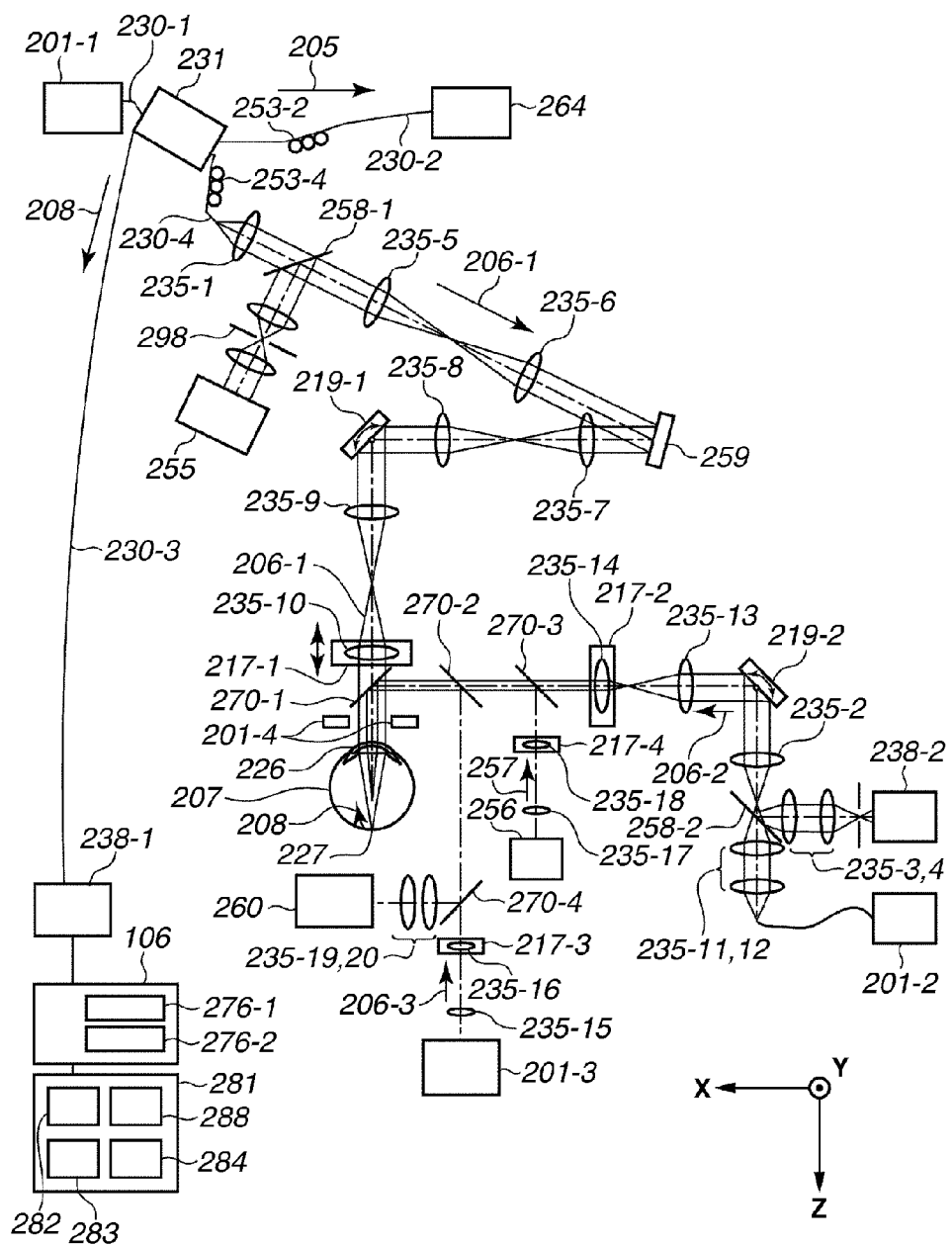
FIG. 2 illustrates a configuration of an optical system of the ophthalmologic imaging apparatus according to the exemplary embodiment.

Next referring to FIG. 2, the optical system included in the head unit 102 will specifically be described.

Light emitted from the light source 201-1 is divided into reference light 205 and imaging light 206-1 by a photocoupler 231. The imaging light 206-1 is for capturing an image of an object. The imaging light 206-1 is guided to a subject's eye 207 that is an observation target via a single mode fiber 230-4, the spatial light modulator 259, an XY scanner 219-1, or a dichroic mirror 270-1. The passage through the spatial light modulator 259 enables acquisition of an image reduced in aberration.

A light flux 257 from a fixation lamp 256 plays a role of prompting fixation or rotation of the subject's eye 207.

The imaging light 206-1, which is converted into reflected or scattered light by the subject's eye 207, reversely travels on an optical path, and enters the detector 238-1 via the photocoupler 231. The detector 238-1 converts the intensity of the return light 208 into a voltage, and a planar image of the subject's eye 207 is formed by using its signal. In the present exemplary embodiment, the entire optical system is configured by using a refractive optical system mainly using a lens. However, the optical system can be configured by a reflective optical system using a spherical mirror in place of the lens.

In the present exemplary embodiment, the reflective spatial light modulator is used as an aberration correction device. However, a transmissive spatial light modulator or a variable-shape mirror can be used.

<Light Source of AOSLO Unit>

Next, a portion around the light source (first imaging light source) 201-1 will be described. The light source 201-1 is a super luminescent diode (SLD), which is a representative low-coherent light source. A wavelength is 840 nm, and a band width is 50 nm. In this case, the low-coherent light source is used to acquire a planar image having limited speckle noise. Any type of a light source can be used as long as it can emit low-coherent light while the SLD is selected, and an amplified spontaneous emission (ASE) or the like can be used.

For the wavelength, near-infrared light is suitable in view of eye measurement. Further, a shorter wavelength is desirable because it affects horizontal resolution of the acquired planar image and, in this case, the wavelength is 840 nm. Other wavelengths can be selected depending on measured portions of the observation target.

The light emitted from the light source 201-1 is divided into the reference light 205 and the imaging light 206-1 at a rate of 90:10 via the single mode fiber 230-1 and the photocoupler 231. The AOSLO apparatus includes a polarization controller 253.

<Reference Optical Path of AOSLO Unit>

Next, an optical path of the reference light 205 will be described.

The reference light 205 divided by the photocoupler 231 enters a light amount measurement apparatus 264 via a optical fiber 230-2. The light amount measurement apparatus 264 is used for measuring an amount of the reference light 205 and monitoring an amount of the imaging light 206-1.

<Imaging Optical Path of AOSLO Unit>

Next, an optical path of the imaging light 206-1 will be described.

The imaging light 206-1 divided by the photocoupler 231 is guided to a lens 235-1 via a single mode fiber 230-4, and adjusted to be parallel light having a diameter of 4 mm.

The imaging light 206-1 passes through a beam splitter 258-1 and lenses 235-5 and 235-6 to enter the spatial light modulator 259.

Then, the imaging light 206-1 is modulated by the spatial light modulator 259, and passes through lenses 235-7 and 235-8 to enter the XY scanner 219-1. For simplicity, the XY scanner 219-1 is a single mirror. In reality, however, two mirrors are arranged close to each other as an X scanner and a Y scanner, and raster scanning is performed on a retina 227 vertically to the optical axis. A center of the imaging light 206-1 is adjusted to coincide with a mirror rotational center of the XY scanner 219-1.

The X scanner scans the imaging light 206-1 in a direction parallel to a paper surface, and a resonance scanner is used. A driving frequency is about 7.9 kHz. The Y scanner scans the imaging light 206-1 in a direction vertical to the paper surface, and a Galvano scanner is used. A driving waveform is a saw-tooth wave, a frequency is about 32 Hz, and a duty ratio is 16%. The driving frequency of the Y scanner is an important parameter for determining a frame rate of a captured AOSLO image.

The XY scanner 219-1 is controlled by the control PC 106 via an optical scanner driver 282 in a driver unit 281.

The lenses 235-9 and 235-10, which are optical systems for scanning the retina 227, play roles of scanning the retina 227 with the imaging light 206-1 with a pupil center of the subject's eye 207 set as a supporting point.

A diameter of the imaging light 206-1 is 4 mm. However, the beam diameter can be larger to acquire an optical image of higher resolution.

An electric stage 217-1 can be moved in an arrow direction illustrated in FIG. 2, i.e., an optical axis direction. A position of the focus lens 235-10 fixed to the electric stage 217-1 is accordingly moved to adjust a focus. Thus, the focus lens 235-10 and the electric stage 217-1 constitute a focusing unit (first imaging light focusing unit) for focusing the imaging light of the AOSLO on the object. The electric stage 217-1 is controlled by the control PC (control apparatus or control unit) 106 via an electric stage driver 283 in the driver unit 281. Adjusting the position of the lens 235-10 enables focusing of the imaging light 206-1 at a position in a specific depth direction in the retina 227 of the subject's eye 207. The apparatus can even deal with refraction abnormality in the subject's eye 207.

Since the imaging light needs to be focused for a position of the imaging target of the fundus, a focusing position is determined according to the position of the imaging target of the fundus in addition to aberration caused by the apparatus and a diopter value of the subject's eye. The focusing position can be set manually by a user interface (UI) described below. However, for example, if the focusing position can be automatically set by disposing a dedicated focus sensor, the adjustment step can be shortened. Further, by using a luminance value or a statistical value of an image acquired by an imaging optical system (WFSLO) different from the AOSLO as illustrated in FIG. 2, automatic focus control can be performed without any dedicated focus lens.

The imaging light 206-1, which has entered the subject's eye 207, is converted into return light 208 by reflection or scattering from the retina 227 to be guided to the optical coupler 232 again, and reaches the detector 238-1 via the single mode fiber 230-3. For the detector 238-1, for example, an avalanche photodiode (APD) or a photomultiplier tube (PMT) that is a high-speed and high-sensitivity optical sensor is used. The detector 238-1 constitutes an imaging unit (first imaging unit) for detecting the return light of the imaging light from the object via the spatial light modulator and the imaging light focusing unit to capture an image of the object.

<Beacon (Aberration Measurement) Unit and Aberration Correction Unit>

Next, a beacon (aberration measurement) unit that measures aberration generated in the subject's eye 207 will be described.

Measuring light 206-3 emitted from the light source 201-3 is guided to the subject's eye 207, which is an observation target, via lenses 235-15 and 235-16, or a dichroic mirror 270-4. A part of the return light 208 from the subject's eye 207 is radiated to the wavefront sensor 255 via a dichroic mirror 258-1 and a pinhole 298, and aberration of the return light 208 generated in the subject's eye is measured.

An electric stage 217-3 can be moved in the arrow direction illustrated in FIG. 2, i.e., the optical axis direction. A position of the focus lens 235-16 fixed to the electric stage 217-3 is accordingly moved to adjust a focus. Thus, the focus lens 235-16 and the electric stage 217-3 function as a focusing unit for focusing the imaging light 206-3 for measuring the aberration on the object. As in the case of the focus lens 217-1 of the AOSLO, the electric stage 217-3 is controlled by the control PC (control apparatus or control unit) 106 via the electric stage driver 283 in the driver unit 281.

The measuring light, which only needs to be focused on the fundus, is determined according to a diopter value of the subject's eye except for aberration caused by the apparatus.

The wavefront sensor 255 constitutes an aberration measurement unit that detects measuring light to measure aberration in the optical path. The wavefront sensor 255 is electrically connected to the control PC 106. The wavefront sensor 255 is a Shack-Hartman wavefront sensor, and a measurement range is −10 D to +5 D. The acquired aberration is expressed by using Zernike polynomial, which indicates aberration at the subject's eye 207. The Zernike polynomial includes a tilt term, a defocus term, an astigmatism term, a coma term, and a trefoil term. A center wavelength of the light source 201-3 is 760 nm, and a wavelength width is 20 nm.

The measuring light 206-3 is, to prevent reflection from a cornea 226, deviated from a center of the subject's eye 207 to enter. The pinhole 298 is installed to block out unnecessary light other than the return light 208, and the return light of the measuring light having passed through the pinhole 298 is detected by the wavefront sensor 255. This can reduce a possibility of detection of light not passing through the fundus of the subject's eye, and thus the aberration can be accurately measured. Further, by disposing the focusing unit of the measuring light, the measuring light appropriately passes through the pinhole 298, and thus the aberration can be accurately measured.

The lenses 235-5 to 235-10 are arranged so that the cornea 226, the XY scanner 219-1, the wavefront sensor 255, and the spatial light modulator 259 can be optically conjugate with one another. Thus, the wavefront sensor 255 can measure the aberration caused by the subject's eye 207.

The spatial light modulator 259 functions as an aberration correction unit that corrects the aberration caused by the subject's eye 207 or the optical system of the apparatus. For example, the spatial light modulator 259, which can modulate a phase of the light by a liquid crystal, compensates for the aberration by canceling the measured aberration. The spatial light modulator 259 is controlled for its state by the control PC 106 via a spatial light modulator driver 288 in the driver unit 281. Accordingly, the imaging light 238-1 and its return light form images on an incident surface of the detector 238-1 in the state where the aberration in the optical path has been compensated for to be reduced. The detector 238-1 detects the return light reduced in influence of aberration, and the image of the object can be captured.

The control PC 106 interlockingly controls the states of the focus lens 235-14 for the measuring light 206-3 and the focus lens 235-10 for the imaging light 206-1 of the AOSLO. The focus position changes depending on the diopter of the subject. However, correspondence can be set between the positions of the focus lenses by taking into consideration the optical system of the aberration measurement and the imaging optical system of the AOSLO. In other words, if one light can be focused according to the diopter of the subject, the position of the other focus lens corresponding to the position of one focus lens is uniquely determined. The correspondence between the states of the focus lenses is stored in the storage unit and, by referring to it as occasion demands, the other focus lens can be adjusted according to adjustment of one focus lens. As a result, time and labor of the adjustment step of imaging preparation can be reduced compared with the case of individual adjustment.

Further, a value of the aberration calculated according to an output from the wavefront sensor 255 functioning as the aberration measurement unit includes a defocus value as described above. The control PC 106 can further control the position of the focus lens 235-10 of the AOSLO according to the defocus value. This two-stage adjustment enables fine adjustment of the focus lens of the AOSLO, which needs more detailed adjustment.

<Entire WFSLO Unit>

The AOSLO apparatus 101 can include a WFSLO unit to capture an image having a field angle wider than that of the AOSLO. Hereinafter, the WFSLO unit will be described.

The WFSLO unit has a configuration basically similar to that of the AOSLO unit. Description of overlapped portions will be omitted.

Imaging light (WFSLO imaging light) emitted from the light source (second imaging light source) 201-2 is guided to the subject's eye 207, which is an observation target, via the lens 235-2, the lenses 235-11 to 235-14, the XY scanner 219-2, and the dichroic mirrors 270-1 to 270-3. The light source 201-2 is an SLD as in the case of the AOSLO unit. A wavelength is 920 nm, and a band width is 20 nm.

<Imaging Optical Path of WFSLO Unit>

Next, an optical path of the imaging light 206-2 will be described.

The imaging light 206-2 emitted from the light source 201-2 is guided to the subject's eye 207, which is an observation target, via the lens 235-2, the lenses 235-11 to 235-14, the XY scanner 219-2, and the dichroic mirror 270.

The X scanner, which is a component of the XY scanner 219-2, scans the imaging light 206-2 in a direction parallel to a paper surface, and a resonance scanner is used. A driving frequency is about 3.9 kHz. The Y scanner scans the imaging light 206-2 in a direction vertical to the paper surface, and a Galvano scanner is used. A driving waveform is a saw-tooth wave, a frequency is 15 Hz, and a duty ratio is 16%. The driving frequency of the Y scanner is an important parameter for determining a frame rate of a WFSLO image.

An electric stage 217-2 can be moved in the arrow direction illustrated in FIG. 2, i.e., the optical axis direction. A position of the focus lens 235-14 fixed to the electric stage 217-2 is accordingly moved to adjust a focus. Thus, the focus lens 235-14 and the electric stage 217-2 constitute a focusing unit (second imaging light focusing unit) for focusing the imaging light of the WFSLO on the object. The electric stage 217-2 is controlled by the control PC (control apparatus or control unit) 106 via the electric stage driver 283 in the driver unit 281.

A diameter of the imaging light 206-2 is 1 mm. However, the beam diameter can be larger to acquire an optical image of higher resolution.

The imaging light 206-2, which has entered the subject's eye 207, is converted into return light 208 by reflection or scattering from the retina 227, and reaches the detector 238-2 via the dichroic mirrors 270-1 to 170-3, the lenses 235-13 to 235-14, the lenses 235-2 to 235-4, the XY scanner 219-2, and the beam splitter 258-2. The detector 238-2 constitutes an imaging unit (second imaging unit) for detecting the imaging light 206-2 of the WFSLO to capture an image having a field angle wider than that of the AOSLO image.

The control PC 106 interlockingly controls the focus lens 234-10 of the imaging light 206-1 of the AOSLO, the focus lens 235-16 of the beacon light (measuring light) 206-3, and the focus lens 235-14 of the imaging light 206-2 of the WFSLO. The focus positions of all the focus lenses change depending on the diopter of the subject. However, since other conditions are almost fixed, the position of the other focus lens corresponding to the position of one focus lens can be determined. Thus, focusing with the AOSLO, the measuring light of the aberration, and the WFSLO can be easily controlled.

<Fixation Lamp>

Figure 7:
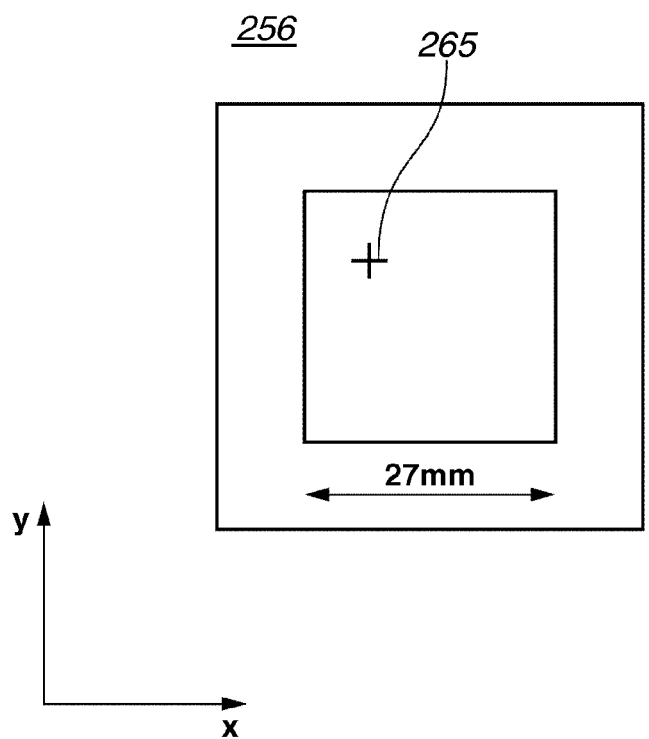
FIG. 7 illustrates a display screen of a fixation lamp according to the exemplary embodiment.

The AOSLO apparatus 101 can include a fixation lamp for fixating the subject's eye. The fixation lamp 256, which includes a light emitting display module, has a display surface (27 mm, 128×128 pixels) on an XY plane. An organic electroluminescence (EL) or a light emitting diode (LED) array can be used. The subject's eye pays close attention to a light flux 257 from the fixation lamp 256, and accordingly fixation or rotation of the subject's eye 207 is prompted. In the display surface of the fixation lamp 256, for example, as illustrated in FIG. 7, a cross pattern is flashed to be displayed at an arbitrary lighting position 265.

The light flux 257 from the fixation lamp 256 is guided to the retina 227 via the lenses 235-17 and 235-18 and dichroic mirrors 270-1 to 270-3. The lenses 235-17 and 235-18 are arranged so that the display surface of the fixation lamp 256 and the retina 227 can be optically conjugate with each other. The fixation lamp 256 is controlled by the control PC 106 via a fixation lamp driver 284 in the driver unit 281.

An electric stage 217-4 can be moved in the arrow direction illustrated in FIG. 2, i.e., the optical axis direction. A position of the focus lens 235-18 fixed to the electric stage 217-4 is accordingly moved to adjust a focus. Thus, the focus lens 235-18 and the electric stage 217-4 constitute a focusing unit for focusing a fixation target of the fixation lamp on the object. The electric stage 217-4 is controlled by the control PC (control apparatus or control unit) 106 via the electric stage driver 283 in the driver unit 281.

The control PC 106 interlockingly controls the focus lens 234-10 for the imaging light 206-1 of the AOSLO, the focus lens 235-16 for the beacon light (measuring light) 206-3, the focus lens 235-14 for the imaging light 206-2 of the WFSLO, and the focus lens 235-18 for the fixation lamp. Thus, focusing with the AOSLO, the measuring light of the aberration, the WFSLO, and the fixation lamp can be easily controlled.

<Anterior Segment Observation Unit>

Next, the anterior segment observation unit will be described.

Light emitted from the anterior segment observation unit 201-4 illuminates the subject's eye 207, and its reflected light enters a charge-coupled device (CCD) camera 260 via the dichroic mirrors 207-1, 207-2, and 207-4 and lenses 235-19 and 235-20. The light source 201-4 is an LED having a center wavelength of 740 nm.

<Focus, Shutter, and Astigmatism Correction>

As described above, the optical system in the head unit 102 includes the AOSLO unit, the WFSLO unit, the beacon unit, the fixation lamp unit, and the anterior segment observation unit. The AOSLO unit, the WFSLO unit, the beacon unit, and the fixation lamp unit individually include the electric stages 217-1 to 217-4, and the four electric stages are interlockingly operated. However, when focus positions are individually adjusted, the positions can be adjusted by individually operating the electric stages.

Especially, the focus lenses of the WFSLO unit, the beacon unit, and the fixation lamp other than the AOSLO can be interlocked because their positions change depending on the diopter of the subject's eye. However, for the AOSLO, the position of the focus lens changes depending on an imaging position of the subject's eye, which is an imaging target, in a depth direction. Thus, for the focus lens 235-10 of the AOSLO, a position can be changed independently from the other focus lenses under control of the control PC 106.

Each of the AOSLO unit, the WFSLO unit, and the beacon unit includes a shutter (not illustrated), and whether to allow light to enter the subject's eye 207 can be individually controlled by opening or closing the shutter. In this case, the shutter is used. However, control can be performed by directly turning ON/OFF the light sources 201-1 to 201-3.

Similarly, the anterior segment observation unit and the fixation lamp unit can be controlled by turning ON/OFF the light source 201-4 and the fixation lamp 256.

The lens 235-10 can be replaceable, and a spherical lens or a cylindrical lens can be used according to the aberration caused by the subject's eye 207. Not limited to one lens, a plurality of lenses can be installed in combination.

<Wavelength>

Figure 3:
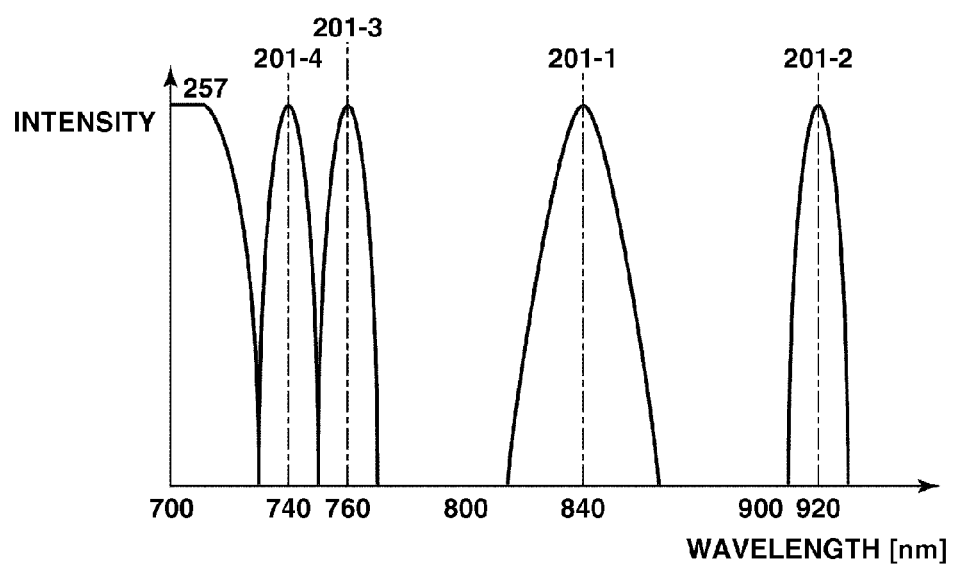
FIG. 3 illustrates a wavelength distribution of light used in an AOSLO apparatus.

FIG. 3 illustrates a wavelength distribution of the light sources used for the AOSLO unit, the WFSLO unit, the beacon unit, the fixation lamp unit, and the anterior segment observation unit. The light beams are divided by the dichroic mirrors 270-1 to 270-4, and thus have different wavelength ranges. FIG. 3, which illustrates a difference in wavelength among the light sources, does not define the intensity or spectral shapes thereof.

<Image Formation>

Next, a configuration method of a captured mage will be described.

For the light entering the detector 238-1, its intensity is converted into a voltage. A voltage signal acquired at the detector 238-1 is converted into a digital value at an AD board 276-1 in the control PC 106. The control PC 106 performs data processing in synchronization with an operation or a driving frequency of the XY scanner 219-1 to form an AOSLO image. A capturing speed of the AD board 276-1 is 15 MHz. Similarly, a voltage signal acquired at the detector 238-2 is converted into a digital value at an AD board 276-2 in the control PC 106, and a WFSLO image is formed.

<Details on Control PC>

Figure 4:
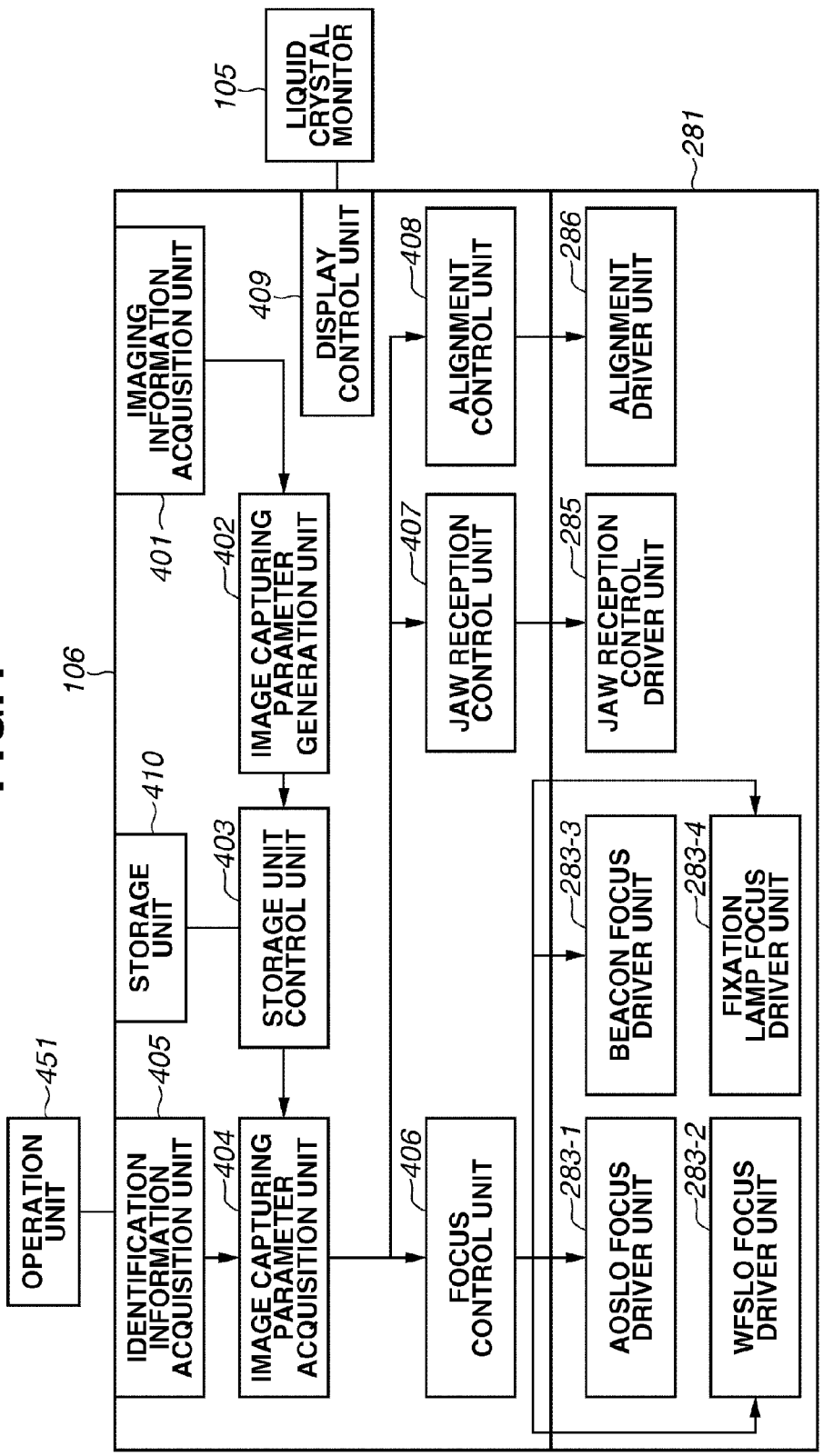
FIG. 4 illustrates a configuration of a control apparatus according to the exemplary embodiment.

Referring to FIG. 4, a configuration concerning reutilization of the imaging condition of the control PC 106 will be described. The control PC includes an imaging information acquisition unit 401, an image capturing parameter generation unit 402, a storage unit control unit 403, an image capturing parameter acquisition unit 404, an identification information acquisition unit 405, a focus control unit 406, a jaw reception control unit 407, an alignment control unit 408, a display unit 409, and a storage unit 410. The control PC 106 is connected to the driver unit 281, an operation unit 451, and a liquid crystal monitor 105. The driver unit 281 includes, as focus driver units, an AOSLO focus driver unit 283-1, a WFSLO focus driver unit 283-2, a beacon focus driver unit 283-3, and a fixation lamp focus driver unit 283-4. The driver unit 281 further includes a jaw reception control driver unit 285 and an alignment driver unit 286.

The imaging information acquisition unit 401 acquires a parameter used for imaging at the AOSLO apparatus 101. For example, the imaging information acquisition unit 401 acquires information about positions of the focus lenses 235-10, 235-14, 135-16, and 235-18, a position of the jaw receiver 108, or a position of the head unit 102, and information about the subject, which is an imaging target. In this case, for example, identification information of the subject of the imaging target, information indicating one of left and right eyes, and information about a name or an age are acquired.

The image capturing parameter generation unit 402 generates, from the parameter used for imaging, an image capturing parameter stored in the storage unit 410 to be used for next imaging. The image capturing parameter includes at least one of the positions of the focus lenses 235-10, 235-14, 135-16, and 235-18, the position of the jaw receiver 108, and the position of the head unit 102. For example, when the positions of the focus lenses are interlockingly controlled, it is enough to generate a position of one of the focus lenses as an image capturing parameter. Needless to say, storing all the pieces of information is useful because time and labor of adjustment can be greatly reduced.

Several seconds may be necessary from starting actual imaging to completion after completion of adjustment for imaging. According to an example, the imaging information acquisition unit 401 acquires an image capturing parameter at timing when a measuring start is instructed. For example, when the focus lens 235-16 for the beacon light (measuring light) 206-3 continuously performs auto-focusing, the imaging information acquisition unit 401 generates (selects) a position of the focus lens 235-16 at timing when measurement is started as an image capturing parameter. According to another example, an image capturing parameter is generated during measurement, after an end of the measurement, completion timing of image recording, or timing of imaging end instruction.

The control PC 106 can continuously monitor an image quality evaluation value of a Hartman image or a WFSLO or AOSLO image to be captured, and the image capturing parameter generation unit 402 can generate an image capturing parameter based on a parameter in a status where a specific criterion is satisfied. For example, if an average value or a median value among parameters when the image quality evaluation value is equal to or higher than a threshold value is stored as an image capturing parameter in the storage unit 410, accurate adjustment can be performed, and a status where a parameter of an imaging failure or unsatisfactory image quality can be reduced. It is similarly useful to generate an image capturing parameter from a parameter when the image quality evaluation value is in the top 10%.

Further, the image capturing parameter generation unit 402 can generate an image capturing parameter from a position during image capturing for the focus lens 235-10 or 235-14 of the AOSLO or the WFSLO. Accordingly, an image capturing parameter can be generated from a position of the focus lens 235-16 of beacon light during image capturing.

In the case of an apparatus that separately executes the aberration measurement step and the AOSLO imaging step, original data of image capturing parameters to be recorded can be acquired at different timings. For example, for the focus lens 235-16 for the beacon light (measuring light) 206-3 concerning the aberration measurement, an image capturing parameter can be generated based on a position during the aberration measurement. For the focus lens 235-10 for the imaging light 206-1 of the AOSLO concerning the imaging, an image capturing parameter can be generated based on a position during capturing of the AOSLO image.

On the other hand, in the case of simultaneously performing aberration measurement and AOSLO imaging in real time, if they are performed by being switched in time division, adjustment using more appropriate image capturing parameters can be carried out by acquiring original data of the image capturing parameters to be stored.

For the position of the focus lens 235-16 for the beacon light and the position of the focus lens 235-18 for the fixation lamp 256, information about a diopter of the subject is a factor to be taken into consideration since the lenses only need to be focused on the fundus. Similarly, for the position of the focus lens 235-14 of the WFSLO, the information about the diopter is a main factor to be taken into consideration for WFSLO focusing because greater accuracy may be unnecessary as long as the lens is focused on the fundus.

In such a case, information stored as an image capturing parameter for these focus lenses in the storage unit 410 can be used as information about the diopter of the subject. Accordingly, the image capturing parameters for a plurality of related focus lenses can be integrated. When fine adjustment is presupposed or an inspector manually performs adjustment, for the position of the focus lens 235-10 of the AOSLO, the information about the diopter of the subject can be a factor to be taken into consideration.

However, for the focus lens 235-10 of the AOSLO, a position of the retina in the depth direction to be focused on must be taken into consideration in addition to the diopter of the subject. Thus, information about an image capturing parameter of the focus lens 235-10 of the AOSLO can be stored in the storage unit 410 in addition to the information about the diopter. The information about the diopter and information about a difference value from the position of the focus lens determined by the diopter can be combined to be used as an image capturing parameter (information indicating position) of the focus lens 235-10. In this case, the image capturing parameter generation unit 402 generates the information about the diopter and the information about the difference value, and the storage unit control unit 403 stores them in the storage unit 410 in association with the identification information of the subject.

The storage unit control unit 403 stores the generated image capturing parameter in the storage unit 410. The generated image capturing parameter is stored in association with the identification information of the subject, which is an imaging target. In addition to the identification information, information about a thumbnail of the acquired image, a measured aberration value, or a difference between left and right eyes of the subject can be stored. The storage unit control unit 403 stores the information about the generated image capturing parameter in the storage unit 410 disposed in the control PC 106. However, the information can be stored outside the control PC 106 or in an external server connected to the AOSLO apparatus 101 via a network.

The image capturing parameter acquisition unit 404 acquires the image capturing parameter corresponding to the identification information from the storage unit 410 by using the identification information of the subject as a search key. Thus, the image capturing parameter acquisition unit 404 constitutes an acquisition unit that acquires the information indicating the position of the focus lens 235-16 of the beacon light (measuring light) corresponding to the identification information of the specific object from the storage unit 410. The image capturing parameter acquisition unit 404 can search in the storage unit 410 via the storage unit control unit 403. However, the image capturing parameter acquisition unit 404 can directly search in the storage unit 410 to acquire the image capturing parameter.

The identification information acquisition unit 405 acquires the identification information of the subject input by the operation unit 451. Each identification information may be data including a set of a name, a sex, and an age of the subject. However, to prevent overlapping, ID information uniquely added to each subject can be acquired as the identification information. The operation unit 451 includes, for example, a graphical user interface (GUI) described below, or an operation device or a touch panel for operating the GUI illustrated in FIG. 5.

The focus control unit 406 gives instructions about movement, a moving amount and a moving direction of the focus lenses to necessary one of the focus drivers 283-1 to 283-4 of the driver unit 281. Accordingly, the focus drivers drive the electric stages 217-1 to 217-4 to move the corresponding focus lenses. Thus, the focus control unit 406 controls the position of the focus lens 235-16 based on the acquired information indicating the position of the focus lens 235-16.

The jaw reception control unit 407 transmits an instruction signal to move the position of the jaw receiver 108 by a specific amount in a specific direction based on the image capturing parameter received from the image capturing parameter acquisition unit 404 to the jaw reception control driver unit 285. The jaw reception control driver unit 285 drives the jaw receiver stage unit 109, and moves the jaw receiver 108 to the position indicated by the instruction signal.

The alignment control unit 408 transmits an instruction signal to move the head unit (a casing of the measurement unit) 102 by a specific amount in a specific direction based on the image capturing parameter received from the image capturing parameter acquisition unit 404 to the alignment driver unit 286. The alignment driver unit 286 drives the stage unit 103, and moves the head unit 102 to the position indicated by the instruction signal.

Thus, the control unit such as the focus control unit 406, the jaw reception control unit 407, or the alignment control unit 408 controls the AOSLO apparatus 110 based on the information about the image capturing parameter stored in the storage unit 410 corresponding to the identification information of the specific object. As a result, adjustment can be easily performed under the imaging conditions prepared beforehand.

Each of the control units can deal, if fine adjustment is performed after adjustment according to a last image capturing parameter, with changes in subject and others made with the passage of time from the last imaging. The focus control unit 406 first moves the focus lens to the position of the focus lens acquired according to the identification information of the subject, and then starts searching for a focusing position of the focus lens with this position set as an initial position. Especially, adjustment conditions are stricter for the focus lens 235-10 of the AOSLO than the other focus lenses. The focus control unit 406 can instruct fine adjustment only for the focus lens 235-10 of the AOSLO. In addition, for the focus lens of the beacon light (measuring light) 206-3, adjustment is necessary to transmit the light through the pinhole 298, and thus there is an advantage of fine adjustment.

An image capturing parameter to be stored and reutilized is not limited to this. For example, the aberration is measured, and the spatial light modulator 259 is set in a state of being able to sufficiently reduce the aberration. Then, the storage unit control unit 403 can store the state of the spatial light modulator 259 in the storage unit 410. The state information of the spatial light modulator 259 is used during imaging of the same object, and used for next imaging. Accordingly, since the state of the spatial light modulator 259 is controlled in a state where the aberration has been reduced to a certain extent, a time necessary for correcting the aberration can be shortened. Further, when tracking is performed to move the imaging range of the AOSLO, thereby cancelling movement of the fundus, the imaging range of the AOSLO, more accurately, the imaging range in a direction orthogonal to the depth direction, can be stored. The imaging range of the AOSLO can be achieved by changing the position of the scanner 219-1.

Figure 5:
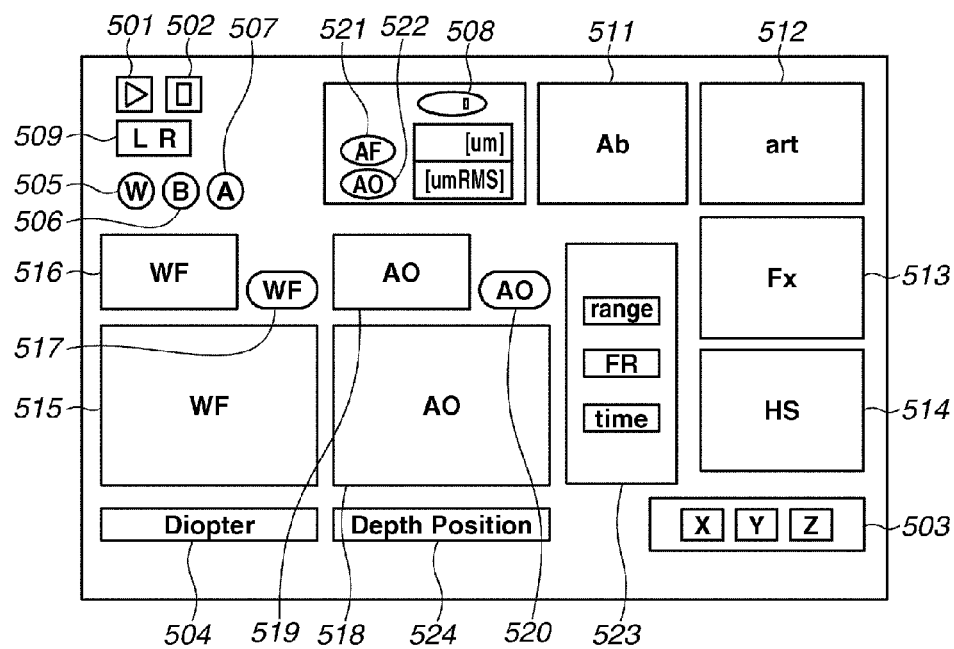
FIG. 5 illustrates a control software screen according to the exemplary embodiment.
Figure 6:
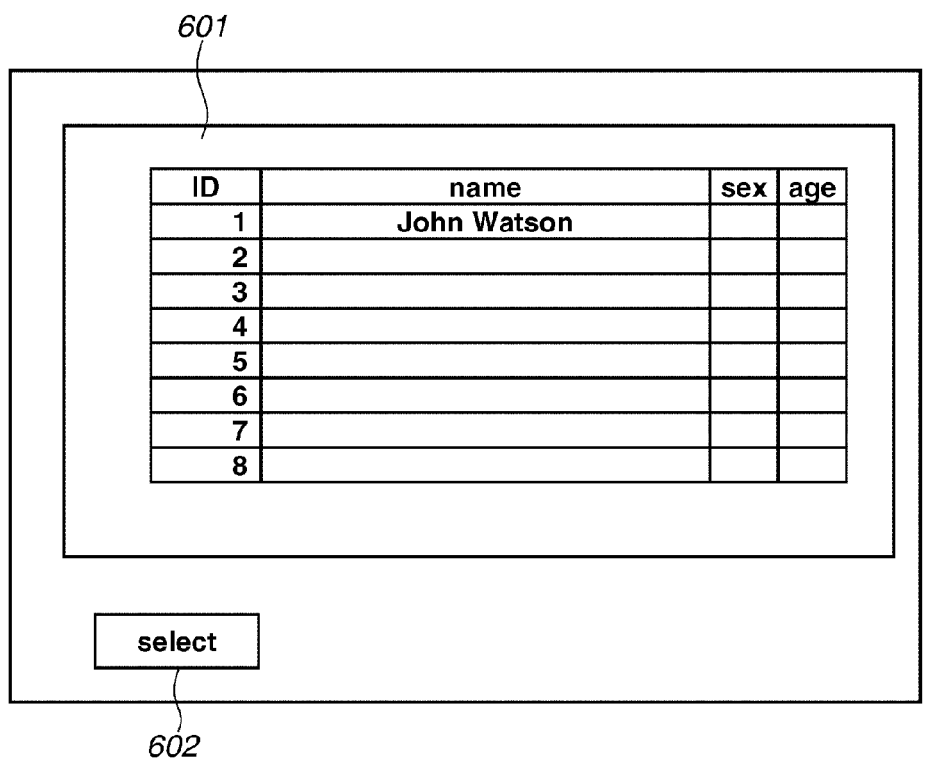
FIG. 6 illustrates an image viewing software screen according to the exemplary embodiment.

The display control unit 409 can display, on the liquid crystal monitor 105 included in the display unit, the GUI for control illustrated in FIGS. 5 and 6.

The storage unit 410, which is a memory of the control PC 106, stores the information of the subject or the image capturing parameter according to an instruction from the storage unit control unit 403.

Each unit of the control PC 106, which can be configured by using a dedicated circuit, can also be configured by using software and the hardware of the control PC 106. In this case, a central processing unit (CPU) of the control PC 106 can function as each unit illustrated in FIG. 4 by rasterizing programs stored in a read-only memory (ROM) to sequentially execute them, and can execute processing described below referring to FIGS. 8 to 10. The programs include image data for forming the GUI illustrated in FIGS. 5 and 6. Appropriate image data is displayed by the display unit based on an instruction executed by the CPU.

<GUI of Control Software>

Referring to FIGS. 5 and 6, the GUI displayed on the liquid crystal monitor 105 by the display control unit 408 will be described. FIG. 5 illustrates an example of a GUI for adjustment before imaging. An execution button 501 is a button for starting imaging of the apparatus. By pressing the button 501, the anterior segment imaging light source 201-4 is lit, and an image detected and captured by the CCD camera 260 is displayed on the anterior segment monitor 512. A stop button 502 is a button for ending the imaging. An electric stage button 503 is a button for moving the jaw receiver, and corresponding buttons are respectively arranged in an X direction, a Y direction, and a Z direction. By pressing the button 503, the jaw receiver driving unit 109 can be finely moved. A button can be disposed to move the head unit 102 in the X, Y, and Z directions.

A focus adjustment button 504 is a button (second instruction unit) for interlockingly moving the focus lens 235-10 of the imaging light 206-1 of the AOSLO, the focus lens 235-16 of the beacon light (measuring light) 206-3, and their focus lenses when a WFSLO and a fixation lamp are present. For example, the focus adjustment button 504 can include a button for moving the focus lens in a first direction and a button for moving the focus lens in a second direction. In response to pressing of the focus adjustment button 504, focus searching can be automatically started.

A WFSLO imaging instruction button 505 is a button for switching ON/OFF of displaying of an image on a WFSLO monitor 515 of the WFSLO image. It can be a button for instructing activation or stop of the scanner or the detector of the WFSLO. Simultaneously with displaying of the image on the WFSLO monitor 515, information indicating the intensity of the WFSLO image is displayed on a WFSLO intensity monitor 516. For example, the signal intensity detected by the WFSLO unit is time-sequentially displayed with a horizontal axis indicating time and a vertical axis indicating the signal intensity. To record the WFSLO image, a recording start is instructed by pressing a WFSLO recording button 517, and a WFSLO moving image is accordingly stored in the storage unit 410. An instruction button for storing a still image or one frame can also be disposed. Further, a button for instructing outputting of one frame to a paper medium by a printer (not illustrated) can be disposed.

If without pressing the WFSLO imaging instruction button 505, WFSLO imaging or image displaying is automatically started according to completion of alignment based on the anterior segment image, operation time and labor can be reduced.

An aberration measurement button 506 is operable for starting emission of the beacon light (measuring light) 206-3, and displaying a Hartman image acquired by the wavefront sensor 255 on a wavefront sensor monitor 504. Aberration calculated from the Hartman image is displayed on an aberration correction monitor 511. The process from the acquisition of the Hartman image to the calculation of the aberration is executed by a module in the wavefront sensor 255. However, the aberration can be calculated from the Harman image by disposing another module. The wavefront sensor 255 sequentially calculates the aberration based on the acquired Hartman image. Thus, when the state of the spatial light modulator 259 is controlled to reduce the aberration, the aberration displayed on the aberration correction monitor 511 varies.

An autofocus button 521 is a button (third instruction button) for adjusting the positions of the focus lenses 235-1, 235-14, 235-16, and 235-18 by using a defocus value acquired by the wavefront sensor 255. In response to pressing of the button, the focus control unit 406 of the control PC interlockingly controls the four focus lenses.

By pressing an aberration correction button 522, the state of the spatial light modulator 259 is automatically controlled to reduce an aberration amount. For example, if imaging of the AOSLO is instructed when the aberration amount is lower than a specific threshold value, operation time and labor are reduced, and quick imaging can be performed.

An aberration correction temporary stop button 508 is a button for temporarily stopping searching for aberration correction when the aberration is not automatically reduced to an appropriate value after the aberration measurement button 506 is pressed.

An AOSLO measurement button 507 is a button for instructing an imaging start of the AOSLO. It can be a button for instructing a displaying start of an image captured by the AOSLO. Accordingly, the shutter of the AOSLO 206-1 is opened, the imaging light 206-1 is radiated to the object, and an AOSLO image reduced in aberration is displayed on an AOSLO intensity monitor 518. Information indicating the signal intensity detected by the detector 238-1 is displayed on an AOSLO intensity monitor 519. For this information, as in the case of the information displayed on the WFSLO intensity monitor 516, the signal intensity detected by the WFSLO unit is time-sequentially displayed with a horizontal axis indicating time and a vertical axis indicating the signal intensity.

A depth adjustment button 524 is a button (second instruction unit) for controlling the focus lens 235-10 of the AOSLO independently from the other focus lenses. The depth adjustment button 524 includes buttons for respectively moving the focus lenses in a first direction and a second direction. In response to pressing of each button, the focus control unit 406 of the control PC 106 changes the position of the focus lens 235-10. Thus, the imaging position of the AOSLO in the depth direction can changed.

An AOSLO recording button 520 is a button for instructing a recording start or end of the AOSLO. A moving image of the AOSLO acquired during the period from the instruction of the recording start to the instruction of the recording end is stored in the storage unit 410.

A fixation lamp position monitor 513 displays a position of the fixation lamp.

An operation condition setting button 523 is a GUI for designating an imaging range, a frame rate, and imaging time. Appropriate imaging conditions can be input.

Thus, inputs from the buttons arranged in the GUI illustrated in FIG. 5 are all received by the control PC 106, and each unit of the AOSLO apparatus is controlled according to the input.

FIG. 6 illustrates an example of a subject selection screen for acquiring subject information from the storage unit 410. On a table 601, a name, a sex, and an age of a subject are listed together with a subject ID. The list includes information about a subject that has been imaged once and information about a subject yet to be imaged but reserved to be imaged. For patient information displayed in the list, the subject information stored in the storage unit 410 is acquired in response to activation of the subject selection screen.

A selection button 602 is a button for selecting a subject started to be imaged. When the selection button 602 is pressed in a selected state of one subject in the list, the identification information acquisition unit 405 of the control PC 106 acquires identification information corresponding to the selected subject. The image capturing parameter acquisition unit 404 checks whether an image capturing parameter corresponding to the identification information has been stored in the storage unit 410. When imaging has been performed once for the subject corresponding to the identification information, and the image capturing parameter corresponding to the identification information has been stored, the image capturing parameter acquisition unit 404 acquires the image capturing parameter from the storage unit 410. The corresponding image capturing parameter information at the time of activation of the subject selection screen can be acquired together with the subject information. Further, in this case, if an outline of past imaging history or a past captured thumbnail image is acquired from the image capturing parameter information in the storage unit 410 to be displayed on the subject selection screen, it is useful because the inspector can be reminded of inspection contents. Further, when imaging has been performed by a plurality of times, these are displayed by category, and a button for selecting which category of imaging is performed can be displayed. If in response to pressing of the button, an image capturing parameter corresponding to the selected imaging category is acquired to be used for next imaging, it is useful.

Thus, by performing imaging through use of the image capturing parameter used for last imaging, adjustment time and labor can be reduced, and adjustment corresponding to an individual difference between the subjects can be performed.

<Imaging Procedure>

Next, an imaging procedure in the AOSLO apparatus of the present exemplary embodiment will be described by using FIG. 8 and the control software GUI illustrated in FIG. 5.

Figure 8:
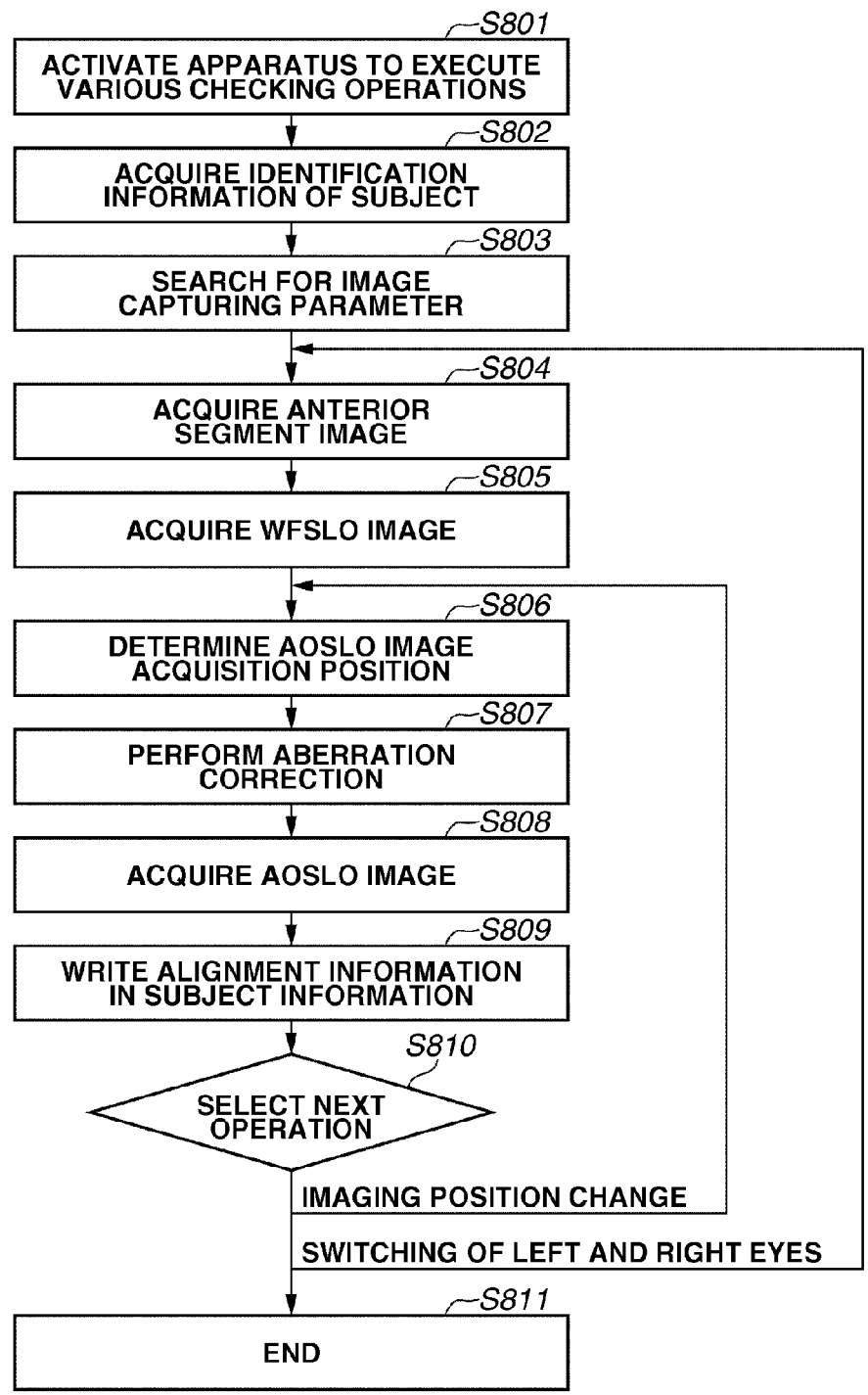
FIG. 8 is a flowchart illustrating an imaging procedure by an SLO apparatus according to the exemplary embodiment.

FIG. 8 illustrates the imaging procedure. Hereinafter, each step will be described in detail.

In step S801, the apparatus is activated to perform various checking operations. Power is turned ON for the control PC 106 and the AOSLO apparatus. Then, the measurement control software is activated to display the control software screen illustrated in FIG. 5 on the liquid crystal monitor 105. The subject sets the face on the face receiver 104.

In step S802, subject information is acquired. When the execution button 501 on the control software screen is pressed, the subject selection screen illustrated in FIG. 6 is displayed. A subject is selected on the table 601, and the selection button 602 is pressed to determine the subject.

When there is no subject information on the table, subject information is registered on the table 601.

In step S803, an image capturing parameter is searched for. After the subject has been selected, the image capturing parameter acquisition unit 404 searches for a corresponding image capturing parameter. When no image capturing parameter can be acquired as a result of the searching, a prescribed initial value can be acquired from the storage unit 410. Alternatively, if initial values are prepared for diagnostic items such as diabetes and age-related macular degeneration, and the values are acquired from the storage unit 410, adjustment can be quickly performed according to the diagnostic items even when there is no image capturing parameter for complete recovery.

In step S804, an anterior segment image is acquired. After a right or left eye has been selected by a subject left/right eye selection button 509 on the control software screen, the control PC 106 calls up a position of the stage unit 103 and positions of the jaw receiver stage unit 109 and the electric stages 217-1 to 217-4 of the focus lenses 235-10, 235-14, 235-16, and 235-18 of the AOSLO unit, the WFSLO unit, the beacon unit, and the fixation lamp unit corresponding to the selected eye stored in the subject information, and drives them to the positions. These positions are positions during last imaging of the selected subject stored in step S810, and a default value of the apparatus is stored at the time of initial imaging.

When each stage is driven, an image of the anterior segment is displayed on the anterior segment monitor 512. When a center of a pupil is not correctly displayed on the screen center, the head unit 102 is first moved to a roughly correct position by using the joystick 107. Further, when adjustment is necessary, the electric stage button 503 on the control screen is pressed to finely move the jaw receiver driving unit 109.

In step S805, a WFSLO image is acquired. When the anterior segment image is displayed roughly in a correct state, the WFSLO image is displayed on the WFSLO monitor 515. The fixation lamp is set in a center position by the fixation lamp position monitor 513, and guided around a line of sight of the subject's eye 207.

Then, while the WFSLO intensity monitor 516 is watched, the focus adjustment button 504 is adjusted to increase the WFSLO intensity. On the WFSLO intensity monitor 516, the signal intensity detected by the WFSLO unit is time-sequentially displayed with a horizontal axis indicating time and a vertical axis indicating the signal intensity. By adjusting the focus adjustment button 504, the positions of the lenses 235-14, 235-16, and 235-18 are simultaneously adjusted.

When the WFSLO image is clearly displayed, the WFSLO recording button 517 is pressed to store WFSLO data.

In step S806, an AOSLO image acquisition position is determined. The displayed WFSLO image is confirmed, and a position for acquiring an AOSLO image is determined by a unit described below. Then, the line of sight of the subject's eye 207 is guided so that the position can be set on the center of the WFSLO monitor 515.

There are two methods for determining an acquisition position of the AOSLO image: one is a method for instructing a position of the fixation lamp on the fixation lamp monitor 513, and the other is a method for clicking a desired position on the WFSLO monitor 515. A pixel on the WFSLO monitor 1515 and the position of the fixation lamp are associated with each other. The position of the fixation lamp is automatically moved, and the line of sight can be guided to a desired position.

After confirmation that the acquisition position of the AOSLO image has moved to the center on the WFSLO monitor 515, the processing proceeds to a next step.

In step S807, aberration correction is performed. When the aberration measurement button 506 is pressed, the imaging light 206-2, which is a WFSLO imaging light, is blocked out, and the shutter of the beacon light is opened to radiate the measuring light 206-3, which is beacon light, to the subject's eye 207. A Hartman image detected by the wavefront sensor 255 is displayed on the wavefront sensor monitor 514. Aberration calculated from the Harman image is displayed on the aberration correction monitor 511. The aberration is divided into a defocus component ($\mu$m) and all aberration amounts ($\mu$m RMS) to be displayed. Since the positions of the focus lenses 235-10 and 235-16 of the AOSLO imaging light and the beacon light have been adjusted in step S804, preparation has been made for aberration measurement at this step. Specifically, the return light 208 of the measuring light 206-3 passes through the pinhole 298 without being kicked off to reach the wavefront sensor 255.

When the autofocus button 521 is pressed, the positions of the lenses 235-10, 235-14, 235-16, and 235-18 are automatically adjusted to reduce a default value.

Then, when the aberration correction button 522 is pressed, the spatial light modulator 259 is automatically adjusted in a direction where an aberration amount is smaller, and a value of the aberration amount is displayed in real time. When the value of the aberration amount is equal to or lower than a predetermined threshold value (0.03 μm RMS), the AOSLO measurement button 507 is automatically pressed, and the processing proceeds to a next step. The threshold value of the aberration amount can be arbitrarily set. When the value of the aberration amount is not equal to or lower than the predetermined threshold value, the aberration correction temporary stop button 508 is pressed to stop the aberration correction. Then, the processing proceeds to a next step by pressing the AOSLO measurement button 507.

In step S808, an AOSLO image is acquired. When the AOSLO measurement button 507 is pressed, the measuring light 206-3, which is beacon light, is blocked out, and the shutter of the AOSLO imaging light 206-1 is opened to radiate the imaging light 206-1 to the subject's eye 207. An aberration-corrected AOSLO image is displayed on the AOSLO monitor 518. On the AOSLO intensity monitor 519, as in the case of the WFSLO intensity monitor 516, the signal intensity detected by the AOSLO is time-sequentially displayed.

When the signal intensity is insufficient, while the AOSLO intensity monitor 519 is watched, a focus and a jaw reception position are adjusted to increase the signal intensity.

By the operation condition setting button 523, an imaging field angle, a frame rate, and imaging time can be designated.

By adjusting the depth adjustment button 524 to move the lens 235-10, an imaging range of the subject's eye 207 can be adjusted. Specifically, an image of a desired layer such as a stratum neuroepitheliale retinae, a nerve fiber layer or a pigmented layer can be acquired.

When the AOSLO image is clearly displayed, the AOSLO recording button 520 is pressed to store AOSLO data. Then, the imaging light 206-1 is blocked out.

In step S809, alignment information is written in the subject information. The position of the stage unit 103 and the positions of the jaw receiver stage unit 109 and the electric stages 217-1 to 217-4 of the focus lenses 235-10, 235-14, 235-16, and 235-18 of the AOSLO unit, the WFSLO unit, the beacon unit, and the fixation lamp unit are written to be stored for the subject's eye selected in step S804 of the subject selected in step S803.

In step S810, a next operation is selected. The processing returns to step S806 when the imaging position is changed, and to step S804 when the left and right eyes are switched. To end the imaging, the processing proceeds to a next step.

In step S810, the processing is ended. When the stop button 502 is pressed, the control software terminates.

Figure 9:
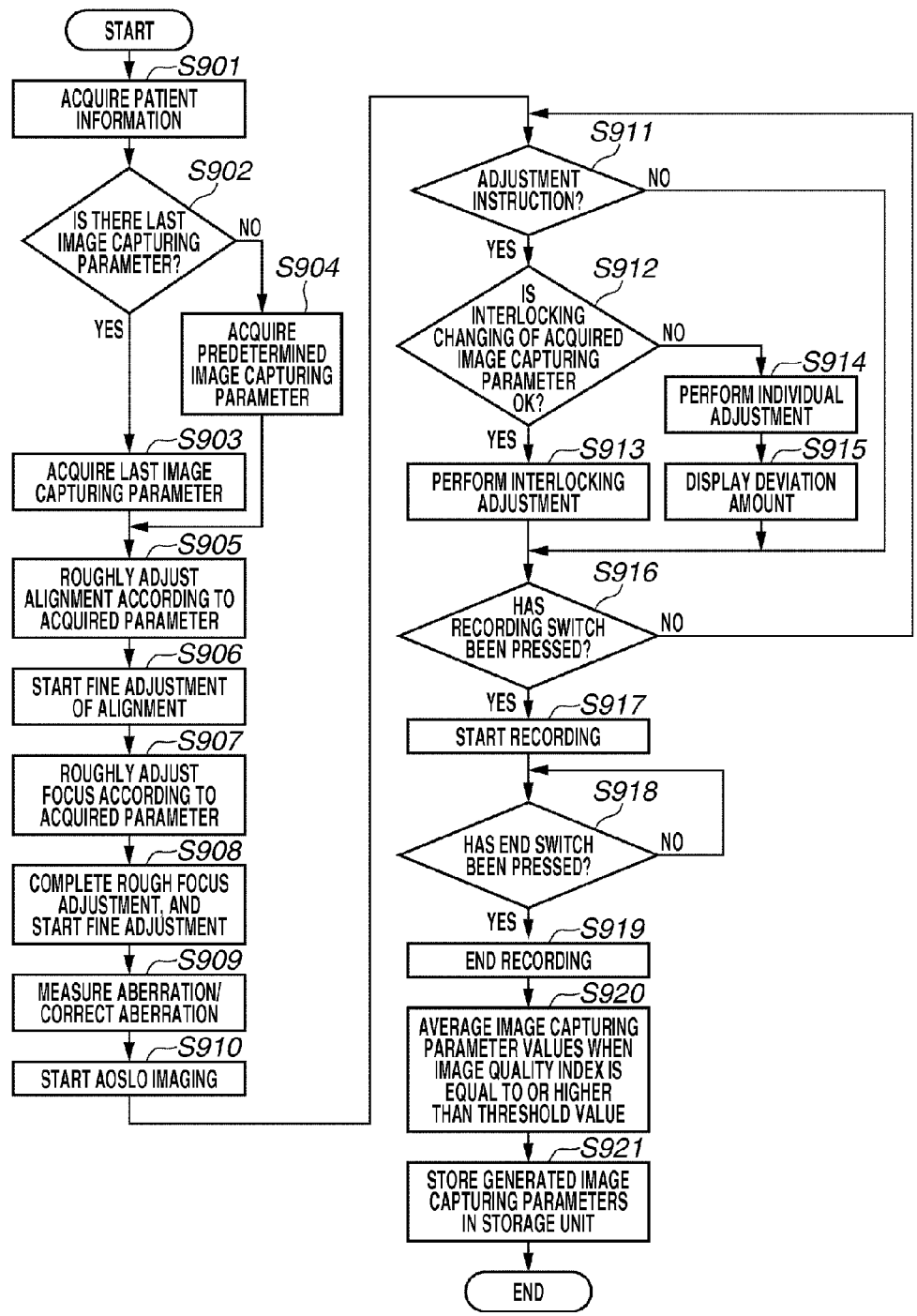
FIG. 9 is a flowchart illustrating a control flow according to the exemplary embodiment.

FIG. 9 is a flowchart illustrating an imaging control flow according to another exemplary embodiment. In this example, many adjustments are automatically performed. Main units of control will be described by taking the example of the control PC 106 illustrated in FIG. 4.

In step S901, the identification information acquisition unit 405 acquires the identification information of the subject from the operation unit 451 such as the GUI. The identification information is ID of the subject selected by the inspector using, for example, the GUI illustrated in FIG. 6. The GUI illustrated in FIG. 6 is displayed in response to pressing of the execution button 501 in the GUI illustrated in FIG. 5. If the display control unit 509 performs control so that the GUI illustrated in FIG. 6 can be automatically displayed at the time of activating the control software or at the end of last imaging, operation time and labor can be reduced.

In step S902, the image capturing parameter acquisition unit 404 searches for an image capturing parameter corresponding to the acquired identification information via the storage unit control unit 403. When it is determined as a result of the searching that there is an image capturing parameter (YES in step S902), the processing proceeds to step S903.

In step S903, the image capturing parameter acquisition unit 404 acquires an image capturing parameter based on information used for last imaging. When a plurality of image capturing parameters has been stored, for example, one image capturing parameter is selected according to user's selection and inputting. When a plurality of imaging operations is performed, such as when bloodstream analysis of the macula lutea (yellow spot), visual cell analysis of the macula lutea, and cribrosa lamina analysis of the optic disk (optic papilla) are continuously performed, a plurality of image capturing parameters can be acquired. In this case, only an image capturing parameter of imaging to be executed first is notified to each control unit, and the remaining image capturing parameters are stored in a temporary memory.

When it is determined as a result of the searching that there is no image capturing parameter (NO in step S902), the processing proceeds to step S904. The image capturing parameter acquisition unit 404 acquires a prescribed parameter as an initial value.

In steps S905 to S912, each of the focus control unit 406, the jaw reception control unit 407, and the alignment control unit 408 performs adjustment before imaging according to a past image capturing parameter. In step S905, the jaw reception control unit 407 instructs movement of the jaw receiver 108 to the acquired position of the jaw receiver 108. The alignment control unit 408 instructs movement of the head unit 102 to the acquired position of the heat unit 102. The jaw reception control driver unit 285 drives the jaw receiver driving unit 109 according to an instruction from the jaw reception control unit 407. The alignment driver unit 286 drives the stage unit 103 according to an instruction from alignment control unit 408.

In step S906, the jaw reception control unit 407 and the alignment control unit 408, which have moved to the positions according to the past image capturing parameter, are fine-adjusted to optimal positions. For example, in the fine adjustment, the image displayed on the anterior segment monitor 512 illustrated in FIG. 5 is analyzed by the control PC 106, and the jaw receiver 108 and the heat unit 102 are moved so that a position and a size of the pupil can be within basic ranges. In step S905, rough adjustment is performed. In step S06, fine adjustment is performed. The fine adjustment is started in step S906, and continues until the end of imaging. This is for canceling an influence of motion of the subject or involuntary eye movement of the subject's eye. Thus, the position of each unit moves adaptively to the subject for a period until the end of imaging. Data storage continues corresponding to the positions of the jaw receiver 108 and the head unit 102.

In step S907, the focus control unit 406 instructs movement of the positions of focus lenses 235-10, 235-14, 235-16, and 235-18 to the acquired positions after a positional relationship between the subject' eye and the head unit 102 has been adjusted. The AOSLO focus driver unit 283-1 moves the electric stage 217-1 according to the instruction from the focus control unit 406. The WFSLO focus driver unit 283-2 moves the electric stage 217-2. The beacon focus driver unit 283-3 moves the electric stage 217-3. The fixation lamp focus driver unit 283-4 moves the electric stage 217-4. Thus, by using the image capturing parameter of the past imaging, imaging preparation time can be shortened, and adaptive adjustment can be easily performed according to the object.

If the adjustment of step S907 is started roughly simultaneously with the start of the fine adjustment of step S906, adjustment time can be shortened.

In step S908, the rough adjustment of the focus lenses 235-10, 235-14, 2135-16, and 235-18 is completed to start fine adjustment. The control PC 106 executes the fine adjustment by using, for example, a dedicated focus sensor. This fine adjustment is started in step S908, and continues until the end of imaging. This is for canceling an influence of motion of the subject or involuntary eye movement of the subject's eye. Thus, the position of each unit moves adaptively to the subject for a period until the end of imaging. The values of the focus lenses are stored corresponding to the positions of the jaw receiver 108 and the head unit 102.

When for the focus adjustment started in step S907, the two-stage adjustment, i.e., the rough adjustment and the fine adjustment, is not performed, step S908 can be omitted.

The control PC 106 starts WFSLO imaging before the start or after the end of the fine adjustment. Further, the control PC 106 calculates image quality index values of the WFSLO image, and time-sequentially stores the values corresponding to the positions of the focus lenses. For the image quality index value, for example, a statistical value such as a size of a luminance value or an average value, or a contrast value can be used.

In step S909, the wavefront sensor 255 starts formation of a Hartman image. The control PC 106 acquires the acquired Hartman image. The display control unit 407 displays the Harman image on the wavefront sensor monitor 514 of the liquid crystal monitor 105. Further, the wavefront sensor 255 sequentially calculates aberration for the acquired Harman image. The control PC 106 acquires the calculated aberration. The display control unit 407 displays the calculated aberration on the aberration correction monitor 511 of the liquid crystal monitor 105. In response to outputting of the calculated aberration value, the control PC 106 changes the state of the spatial light modulator 259 via the spatial light modulator driver 288 in the driver unit 281. The control PC 106 controls a phase difference generated by the spatial light modulator 259 to reduce the calculated aberration.

The control of the spatial light modulator is performed corresponding to, among aberrations, an item other than a defocus item. The defocus item is compensated for by changing the position of the focus lens. The focus control unit 406 changes the position of the AOSLO focus lens 235-10 according to a defocus value. The focus control unit 406 interlocks the focus lens 235-16 of the beacon light (measuring light) with the position of the AOSLO focus lens 235-10.

The control PC 106 time-sequentially stores acquired aberration values corresponding to the positions of the focus lenses.

To start AOSLO imaging in step S910, the shutter for blocking out the light of the light source 201-1 for the imaging light 206-1 is opened, the scanner 219-1 is driven, and the detector 238-1 starts imaging driving. Accordingly, an image of the object is captured with return light of the imaging light 206-1 having passed through the spatial light modulator 259 and the focus lens 235-10. Imaging start timing of the AOSLO can be before or after the start of aberration measurement and correction.

The control PC 106 calculates image quality index values of the AOSLO image, and time-sequentially stores the values corresponding to the positions of the focus lenses. For the image quality index value, for example, a statistical value such as a size of a luminance value or an average value, or a contrast value can be used.

The processing of steps S911 to S915 is manual adjustment performed according to an inspector's wish in addition to the autofocus control. The control PC 106 determines whether a focus control instruction has been acquired. The processing proceeds to step S916 when there is no instruction (NO in step S911). The processing proceeds to step S912 when there is an instruction (YES in step S911).

In step S912, the control PC 106 determines whether the control instruction received in step S911 is an instruction to perform individual movement of only one focus position independently from the other focus lenses. For example, the control PC 106 determines this based on which of a control instruction by pressing of the focus adjustment button 504 and a control instruction by pressing of the depth adjustment button 524 the instruction is. When interlocking changing is OK (YES in step S912), then in step S913, interlocking adjustment is performed for the plurality of focus lenses. When interlocking changing is not OK (NO in step S912), then in step S914, individual adjustment is performed for the focus lenses.

Especially, the processing of individually controlling the AOSLO focus positions to move them to target imaging positions (in depth direction) can be automatically performed. For example, when an imaging position is determined for the purpose of observing a visual cell, the control PC 106 determines whether a peak appears in a specific frequency component corresponding to a repeated pattern of the visual cell for a frequency image of the AOSLO image. The camera can be automatically focused on a position for acquiring a visual cell image by performing the determination while moving the focus position of the AOSLO. In addition, the focus can be automatically adjusted by determining appearance of a characteristic pattern of the target imaging position. Further, a rough position of the fundus taking a working distance or an axial length into consideration can be understood based on a focusing position of the beacon light (measuring light) or the WFSLO. Thus, to capture an image of a choroid membrane side, the camera is focused on a position deep by an experimentally calculated specific value (first value). To capture an image of a vitreous body side, the camera is focused on a position shallow by an experimentally calculated specific value (second value). Thus, by controlling the state of the focus lens 235-10 according to the imaging position of the object in the depth direction, the focus of the AOSLO can be automatically adjusted in the target imaging position or a position near it.

When the individual adjustment is performed in step S915, the display control unit 409 causes the GUI illustrated in FIG. 5 to display a deviation amount when the adjustment is interlocked with the liquid crystal monitor 105. Accordingly, the deviation amount from the normal case can be notified to the inspector in an easily understood manner.

In step S916, the control PC 106 stands by until pressing of the AOSLO recording button is input. When it is determined that the recoding switch has not been pressed (NO in step S916), standing-by for the manual adjustment instruction of step S911 and standing-by for a recording instruction are repeated. When an AOSLO image having aberration reduced equal to or lower than a reference value, recording is automatically started under control of the control PC 106, a high-definition fundus image can be easily acquired. As another example, processing of constantly recording AOSLO images and deleting the recorded AOSLO images during periods other than an instructed period can be applied. This can reduce a possibility that even if the AOSLO images having aberration sufficiently reduced have been captured, they cannot be recorded without any recording instruction.

In step S917, the control PC 106 starts recording according to a recording start instruction.

In step S918, the control PC 106 waits for a recording end instruction. The recording end instruction is issued in response to pressing of the AOSLO recording button 520 again in a pressed and recording state of the AOSLO recording button 520. In step S919, the control PC 106 ends the recording according to the recording end instruction.

In step S920, the imaging information acquisition unit 401 acquires identification information of the imaged subject and information about positions of the jaw receiver 108, the head unit 102, and the focus lenses 235-10, 235-14, 135-16, and 235-18. Then, the image capturing parameter generation unit 402 calculates an average among image capturing parameters when image quality indexes are equal to or higher than the threshold value to set it as an image capturing parameter. A WFSLO image quality index, an AOSLO image quality index, and an aberration value are time-sequentially stored together with the positions of the focus lenses, the jaw receiver, and the head unit. For the image quality indexes, the time-sequentially stored image quality indexes can be used.

In step S921, the storage unit control unit 403 stores the generated image capturing parameter together with the identification information of the subject and left/right eye information in the storage unit 410. In this step, for example, information indicating a position of the focus lens 235-16 for focusing the measuring light 206-3 on the object when aberration is measured is stored in the storage unit 410 in association with the identification information of the subject. Further, for example, at least one of information indicating a position of the head unit (measurement unit) of the AOSLO apparatus 101, information indicating a position of the jaw receiver 108, information indicating a state of the focus lens 235-16 for focusing the measuring light 206-3 for measuring aberration on the subject's eye, information indicating a state of the focus lens 235-10 for focusing the imaging light 206-1 for capturing an AOSLO image, and information indicating a state of the focus lens 235-14 for focusing the imaging light 206-2 for capturing a WFSLO image (second image) having a field angle wider than that of the AOSLO image when the AOSLO image (first image) is captured is stored in the storage unit 410 in association with the identification information of the subjects' eye.

Thus, the stored image capturing parameter can be used at next imaging adjustment, and imaging preparation time and imaging cycle time can be shortened.

The combinations of the exemplary embodiments are within the present invention. For example, as an example of the focusing unit, the focus lens movable along the optical axis has been used. However, a mirror can be used to adjust an in-focus state. The information indicating the state of the focusing unit can be a position of the focus lens in the optical axis or a state of the mirror for adjusting an in-focus state.

An exemplary embodiment where a part of the present invention is realized by cooperation of a program with hardware is also within the invention. According to the exemplary embodiment of the program, a program corresponding to the processing illustrated in FIGS. 8 and 9 and a program corresponding to the display surface illustrated in FIGS. 5 and 6 are stored in the storage unit 410, and the CPU of the control PC 106 loads the programs into the RAM to execute commands included in the programs.

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-126195 filed Jun. 1, 2012, which is hereby incorporated by reference herein in its entirety.

What is claimed is:

1. A measurement apparatus for measuring aberration based on return light of measuring light radiated to an object, the measurement apparatus comprising:
   a light source configured to emit the measuring light;
   a focusing unit configured to focus the measuring light on the object;
   an acquisition unit configured to acquire, from a storage unit, information indicating a state of the focusing unit corresponding to identification information of a specific object; and
   a control unit configured to control the focusing unit based on the acquired information indicating the state of the focusing unit.

2. The measurement apparatus according to claim 1, wherein the control unit starts searching for a focusing position by setting the state of focusing unit indicated by the information as an initial position of the focusing unit.

3. The measurement apparatus according to claim 1, further comprising:
   an aberration measurement unit configured to measure aberration based on the measuring light having passed through the focusing unit; and
   a storing unit configured to store, in the storage unit, the information indicating the state of the focusing unit when the aberration is measured in association with identification information of the object.

4. The measurement apparatus according to claim 3, wherein the control unit continuously controlling the focusing unit, and
   wherein the measurement apparatus further comprises a generation unit configured to generate the information indicating the state of the focusing unit to be stored based on a state of the focusing unit when a value of the measured aberration satisfies a specific criterion.

5. The measurement apparatus according to claim 3, further comprising an adaptive optical system configured to correct the aberration based on the aberration measured by the aberration measurement unit,
wherein the storing unit stores, in the storage unit, a state of the adaptive optical system after the state has been changed based on the measured aberration in association with the identification information of the object.

6. The measurement apparatus according to claim 3, further comprising:
an imaging light source configured to irradiate a subject's eye with light for capturing an image;
an imaging light focusing unit configured to focus the light from the imaging light source on the subject's eye; and
an imaging unit configured to detect the light from the imaging light source having passed through the imaging light focusing unit to acquire an image of the object,
wherein the storing unit stores, in the storage unit, a state of the imaging light focusing unit when the image is captured in association with the identification information of the object.

7. The measurement apparatus according to claim 5, further comprising:
a first imaging light source configured to irradiate a subject's eye with first light for capturing a first image;
a first imaging light focusing unit configured to focus the light from the first imaging light source on the subject's eye;
a first imaging unit configured to detect the light from the first imaging light source having passed through the adaptive optical system and the first imaging light focusing unit to acquire a first image of the object;
a second imaging light source configured to irradiate the subject's eye with second light for capturing an image having a field angle wider than that of the first image; and
a second imaging light focusing unit configured to focus the light from the second imaging light source on the subject's eye; and
a second imaging unit configured to detect the light from the second imaging light source having passed through the second imaging light focusing unit to acquire a second image of the object,
wherein the storing unit stores, in the storage unit, a state of the first imaging light focusing unit when the first image is captured and a state of the second imaging light focusing unit when the second image is captured in association with the identification information of the object.

8. The measurement apparatus according to claim 6, wherein the storing unit stores, in the storage unit, the state of the focusing unit when the image is captured in association with the identification information of the object.

9. The measurement apparatus according to claim 1, wherein the object includes a fundus of a subject.

10. The measurement apparatus according to claim 9, further comprising an adjustment unit configured to adjust a position of a head of the subject,
wherein the storing unit stores, in the storage unit, a position of the adjustment unit during the measurement in association with the identification information of the object.

11. The measurement apparatus according to claim 9, wherein the storing unit stores, in the storage unit, information about a diopter of the subject's eye as the information indicating the state of the focusing unit.

12. The measurement apparatus according to claim 3, further comprising a changing unit configured to change a position of the measurement unit including at least the light source and the focusing unit with respect to the object,
wherein the storing unit stores, in the storage unit, the position of the measurement unit during the measurement in association with the identification information of the object.

13. The measurement apparatus according to claim 3, wherein the control unit performs control based on the information stored by the storing unit corresponding to the identification information of the specific object.

14. The measurement apparatus according to claim 1, wherein the focusing unit includes a focusing lens movable along an optical axis,
wherein the acquisition unit acquires a position of the focusing lens on the optical axis as the information indicating the state of the focusing unit, and
wherein the control unit moves the focusing lens along the optical axis based on the acquired position.

15. An ophthalmologic imaging apparatus comprising:
a measuring light focusing unit configured to focus measuring light radiated to a subject's eye on the subject's eye;
an aberration measurement unit configured to measure aberration based on return light of the measuring light having passed through the measuring light focusing unit;
an adaptive optical system configured to correct the aberration based on the aberration measured by the aberration measurement unit;
a first imaging light source configured to irradiate the subject's eye with first light for capturing a first image;
a first imaging light focusing unit configured to focus the light from the first imaging light source on the subject's eye;
a first imaging unit configured to detect the light from the first imaging light source having passed through the adaptive optical system and the first imaging light focusing unit to acquire a first image of an object;
a second imaging light source configured to irradiate the subject's eye with second light for capturing an image having a field angle wider than that of the first image;
a second imaging light focusing unit configured to focus the light from the second imaging light source on the subject's eye;
a second imaging unit configured to detect the light from the second imaging light source having passed through the second imaging light focusing unit to acquire a second image of the object;
a housing configured to store the measuring light focusing unit, the aberration measurement unit, the adaptive optical system, the first and second imaging light sources, the first and second imaging light focusing units, and the first and second imaging units;
a changing unit configured to change a position of the housing;
a jaw receiver configured to adjust a position of a head of the subject; and
a storing unit configured to store, in a storage unit, at least one of a state of the measuring light focusing unit, a state of the first imaging light focusing unit, a state of the second imaging light focusing unit, the position of the housing, and a position of the jaw receiver when the first image is captured in association with identification information of the subject's eye.

16. The ophthalmologic imaging apparatus according to claim 15, wherein the storing unit stores, in the storage unit, the state of the measuring light focusing unit, the state of the first imaging light focusing unit, the state of the second imaging light focusing unit, the position of the housing, and the position of the jaw receiver when the first image is captured in association with the identification information of the subject's eye.

17. The ophthalmologic imaging apparatus according to claim 16, wherein the storing unit stores, in the storage unit, information about a diopter of the subject's eye as information indicating the state of the second imaging light focusing unit, and information indicating the state of the first imaging light focusing unit in addition to the information about the diopter.

18. A method for controlling an apparatus for measuring aberration based on return light of measuring light radiated to an object, the method comprising:
- storing, in a storage unit, information indicating a state of a focusing unit configured to focus the measuring light on the object when the aberration is measured in association with information of a subject;
- acquiring identification information of the object;
- acquiring, from the storage unit, information indicating a state of the focusing unit associated with the object by using the acquired identification information of the object; and
- controlling focusing of the measuring light based on the acquired information indicating the state of the focusing unit.

19. A method for controlling an ophthalmologic imaging apparatus including a measurement unit configured to change a position for capturing a first image of a subject's eye irradiated with light having passed through an aberration correction device for correcting aberration to be imaged and capturing a second image having a field angle wider than that of the first image, and a jaw receiver configured to adjust a position of a head of the subject, the method comprising:
- storing, in a storage unit, at least one of information indicating a position of the measurement unit of the ophthalmologic imaging apparatus, information indicating a position of the jaw receiver, information indicating a state of a focusing unit configured to focus measuring light for measuring aberration on the subject's eye, information indicating a state of a focusing unit configured to focus imaging light for capturing the first image, and information indicating a state of a focusing unit configured to capture the second image having the field angle wider than that of the first image when the first image is captured in association with identification information of the subject's eye;
- acquiring, from the storage unit, the information associated with the subject's eye by using identification information of a specific subject's eye; and
- controlling each unit of the ophthalmologic imaging apparatus based on the information.

20. A non-transitory computer-readable storage medium storing a program that causes a computer to execute the method according to claim 18.

* * * * *